(12) United States Patent
Pestotnik et al.

(10) Patent No.: US 7,705,727 B2
(45) Date of Patent: Apr. 27, 2010

(54) SYSTEM, METHOD, AND COMPUTER PROGRAM FOR INTERFACING AN EXPERT SYSTEM TO A CLINICAL INFORMATION SYSTEM

(75) Inventors: Stanley L. Pestotnik, Sandy, UT (US); William J. Ketcherside, Jr., Kansas City, MO (US); Jonathan B. F. Olson, Salt Lake City, UT (US); William F. Harty, Salt Lake City, UT (US); Robert R. Hausam, Midvale, UT (US); Michael E. Baza, Woods Cross, UT (US)

(73) Assignee: TheraDoc, Inc., Salt Lake City, UT (US)

( * ) Notice: Subject to any disclaimer, the term of this patent is extended or adjusted under 35 U.S.C. 154(b) by 230 days.

(21) Appl. No.: 11/747,817

(22) Filed: May 11, 2007

(65) Prior Publication Data
US 2007/0213602 A1 Sep. 13, 2007

Related U.S. Application Data

(63) Continuation of application No. 10/773,106, filed on Feb. 5, 2004, now Pat. No. 7,230,529.

(60) Provisional application No. 60/445,889, filed on Feb. 7, 2003.

(51) Int. Cl.
*G08B 1/00* (2006.01)

(52) U.S. Cl. .................... 340/539.12; 702/2; 702/3
(58) Field of Classification Search ............ 340/539.12, 340/286.02; 702/2, 3
See application file for complete search history.

(56) References Cited

U.S. PATENT DOCUMENTS 5,517,405 A * 5/1996 McAndrew et al. ........... 706/45

FOREIGN PATENT DOCUMENTS

WO WO 00/07339 9/2000

OTHER PUBLICATIONS

EPO Supplementary Search Report from European Application No. 04709070.9, dated Sep. 23, 2009, 5 pages.

(Continued)

*Primary Examiner*—Daryl C Pope
(74) *Attorney, Agent, or Firm*—Workman Nydegger

(57) ABSTRACT

A method and computer program for interfacing an expert system to a clinical information system. Embodiments of the invention provide tight integration of the systems permitting a clinician to use the functionality provided by the expert system without specifically maintaining separate patient data. They provide a method for communication between the expert system and one or more clinical information systems. This communication permits flow of information and actions between the expert system and the clinical systems and allows maintenance of audit logs in both systems.

28 Claims, 9 Drawing Sheets

OTHER PUBLICATIONS

Muller, et al.: "Towards integration of clinical decision support in commercial hospital information systems using distributed, reusable software and knowledge components," International Journal of Medical Informatics, Elsevier Scientific Publishers, Shannon, Ireland, vol. 64, No. 2-3, pp. 369-377.

Sujansky, et al.: "Bridging the Representational Heterogeneity of Clinical Databases," AAAI Technical Report SS-94-01 [Online] 1994, retrieved from the Internet: URL:http//www.aaai.org/Papers/Symposia/Spring/1994/SS-94-01/SS94 -01-034.pdf [retrieved Sep. 9, 2009].

Xu, et al.: "Integration of medical applications: the 'mediator servie' of the SynEx platform," International Journal of Medical Informatics, Elsevier Scientific Publishers, Shannon, Ireland, vol. 58-59, Sep. 1, 2000, pp. 157-159.

Van De Velde, R.: "Framework for a clinical information system," International Journal of Medical Informatics, Elsevier Scientific Publishers, Shannon, Ireland, vol. 57, No. 1, Jan. 1, 2000, pp. 57-72.

\* cited by examiner

SYSTEM, METHOD, AND COMPUTER PROGRAM FOR INTERFACING AN EXPERT SYSTEM TO A CLINICAL INFORMATION SYSTEM

CROSS-REFERENCE TO RELATED APPLICATIONS

This application is a continuation of U.S. patent application Ser. No. 10/773,106, filed Feb. 5, 2004 now U.S. Pat. No. 7,230,529, which claims the benefit of U.S. Provisional Application No. 60/445,889, filed Feb. 7, 2003. Both applications are herein incorporated by reference in their entirety.

BACKGROUND OF THE INVENTION

1. The Field of the Invention

This invention generally relates to facilitating communication between a clinical system and a separate expert system. More specifically, the present invention relates to systems, methods, and computer programs that provide an interface between a clinical system and a separate expert system.

2. The Relevant Technology

Clinical information systems and electronic medical records systems have been used in patient care for many years. These systems contain a database or repository of data related to the users and administrative functions of the system, as well as a history of clinical results and activities (clinical data functions). They are used as a medical record, for financial transactions related to care, and as a tool for the ongoing clinical treatment of the patient. However, historically, these systems have been built as Online Transaction Processing (OLTP) systems. As a result, they do not contain a great deal of medical or scientific knowledge, and are not designed to provide expert recommendations, (i.e. perform expert functions).

Some clinical information systems have been built with alerting mechanisms and rule-based event monitors embedded within them to provide expert recommendations based on clinical data entered in the system. These systems do not require specific system interfaces between different modules performing the clinical data functions and the expert functions because the clinical data functions and expert functions are embodied in a common system. The need for rapid processing of transactions has limited the power of this model, and in turn has limited the type of expert advice which can be generated. In addition, a user is limited to the features provided by the specific expert system embedded within the common system that has been developed or purchased. There is no opportunity to combine a different expert system within the clinical system itself.

Online Analytic Processing Systems have been developed to provide optimal analytic expert functions. However, these are separate from clinical systems, and while they may have inbound data connection from clinical systems to populate their databases, there is no flow of information back to the clinical system, nor is there an interactive mechanism between the two systems which allows users to move seamlessly between the two types of functionality. These systems are generally used for administrative or case management purposes, rather than direct clinical care. The knowledge embedded and the recommendations made are not directly actionable.

Expert systems have been developed as stand-alone systems, and have been shown to provide valuable information that has the potential to improve medical care. However, their separate nature has limited their usefulness as well. Systems that require the user to enter a separate application are less likely to be used, and those that require the user to enter clinical information that already resides in clinical systems place an additional burden on the user. In addition, they risk loss of data fidelity (or accuracy) because reentered data may be incomplete or in error. The separate nature of these stand-alone systems has thus limited their usefulness and their adoption in clinical practice.

Stand-alone expert systems have not been integrated into clinical systems for a number of reasons. First, comprehensive Electronic Medical Record (EMR) systems are found in very few health systems. Those few sites that have such Electronic Medical Record systems have often developed them in house, and have developed decision support and expert systems within the Electronic Medical Record system itself.

Separate expert systems have been developed for a number of focused clinical areas, but without an Electronic Medical Record system in place, integration was not possible. In addition, there are many technical barriers to an integrated system. First, many Electronic Medical Records have been developed with proprietary operating systems and databases. These systems are difficult if not impossible to integrate with unrelated systems. Second, there is a lack of standards for data and knowledge representation. This makes it difficult to transfer data that could be properly interpreted and manipulated. Even with interface standards that define the structure of messages between systems, the content of the messages may be useless without a common vocabulary.

Commercial systems have also not been developed which integrate stand-alone expert systems with clinical Electronic Medical Records. The business model of Electronic Medical Record vendors is to provide comprehensive solutions to health systems. They differentiate themselves by virtue of the functionality in their expert systems. These systems are integral to their products, and they are not developed to work with the Electronic Medical Record of another vendor. This has discouraged development of independent expert systems that are designed to integrate broadly. Vendors of small niche expert systems have focused on specific areas of functionality such as case management, insurance certification of appropriateness of care, and data analysis. Direct care clinicians do not generally use these systems, and so integration with the Electronic Medical Record has not been pursued.

Finally, the conventional wisdom and teaching of the medical informatics literature has discouraged separate expert systems. Because of the problems with performance, security, vocabulary inconsistencies, and control over development, the widely stated belief has been that expert systems can only be effective when they are built directly into clinical systems. The result of this teaching has been to encourage the development of expert systems that are built into clinical systems, and no attention has been paid to developing a system or method to permit an independent expert system to function in an integrated fashion.

BRIEF SUMMARY OF THE INVENTION

The present invention generally relates to systems, methods, and computer programs that integrate a stand-alone expert system with one or more independent clinical systems. This method allows the stand-alone expert system to be developed and executed independently, and to then be integrated with one or more clinical systems via a set of defined interfaces. There is at least one interface directed into the expert system, and one interface directed out of the expert system to the clinical system. The method allows the expert system to have access to clinical data without requiring separate input by users, and thus preserves data fidelity. It also allows the user to access the expert system from within each of the clinical systems to which it may communicate, and provides seamless movement between the systems. Functionally, the expert system behaves as if it is built intrinsic to the clinical system, although it is actually independent. This complements the clinician's existing workflow, and increases the likelihood that clinicians can use the expert system.

One embodiment of the present invention includes a system for facilitating communication between a standalone medical expert system and at least one clinical system, the system including a standalone medical expert system remote from the clinical system. Without the present invention, the expert system communications may be incompatible with the clinical system or one of its associated clinical modules. Communicating with the expert system and the clinical system is at least one interface module that facilitates transmission of the data between the expert system and the clinical system. The interface module(s) also enable a user of the clinical system to seamlessly access and use the functionality of the medical expert system from within a user interface of the clinical system, with the expert system at least partially controlling the functionality of the clinical system. By so doing, a clinician, physician, or technician uses a clinical module, such as but not limited to, a CDR module, an ADT module, a laboratory module, a pharmacy module, a radiology module, or Electronic Medical Record module, that can access the independent and separate expert system without manually switching applications, re-entering data, or otherwise having the graphical user interface presented by one or more of the clinical modules or the clinical system.

In another embodiment of the present invention, at least one interface module includes or functions as one of a variety of different interfaces, such as but not limited to, an Inbound Data Interface, an Outbound Alert Interface, Outbound Order Interface, Outbound Data Interface, Inbound Application Interface, a Synchronous Alert Interface, or an Audit Action Interface.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE EXEMPLARY EMBODIMENTS

Figure 1:
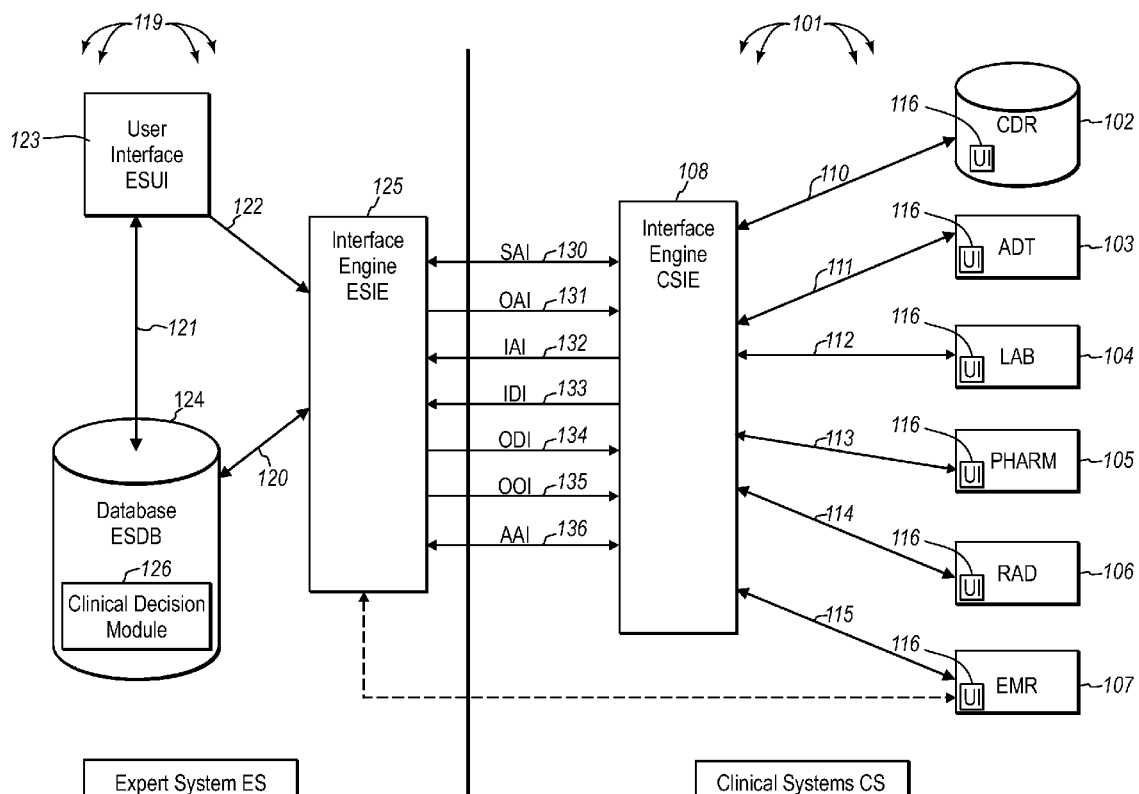
FIG. 1 illustrates a schematic diagram of one exemplary embodiment of the present invention, representing one model of interface implementation between a clinical system and an expert system.

Referring now to FIG. 1, a Clinical System (CS) 101 includes, in one exemplary embodiment, a number of clinical modules including a Clinical Data Repository (CDR) 102, an Admission, Discharge, Transfer (ADT) system 103, a laboratory (LAB) system 104, a pharmacy (PHARM) system 105, a radiology (RAD) system 106, an Electronic Medical Record (EMR) 107, and a Clinical System Interface Engine (CSIE) 108. The clinical modules of the Clinical System 101 shown in FIG. 1 are not exhaustive, nor are all the clinical modules required for embodiments of the present invention. Rather, the modules, systems, interfaces, and databases shown in FIG. 1 are illustrative of one exemplary embodiment of the invention. The clinical modules may be themselves clinical systems as that term is understood in the art. Thus, as used herein, a clinical system may refer to individual clinical modules or to a collection of clinical modules.

Each of the clinical modules may include a user interface (UI) 116 that displays information to a user and accepts data input from the user. The information displayed may be stored, for example in the Clinical Data Repository 102, or in one of the clinical modules to which the information applies. Similarly, data input through the 116 is directed to the Clinical Data Repository 102 or to a repository at a clinical module to which the information applies. The UI 116 can be one of a variety of graphical user interfaces that provides visual representations of the data and allows additional data to be input or entered into the Clinical Data Repository 102. Various frames, fields, menus, images, and text may be used as part of the UI 116.

The Clinical System Interface Engine 108 receives feeds of data 110, 111, 112, 113, 114, 115, from each of the clinical modules. In turn, the Clinical System Interface Engine 108 provides the data to the Expert System 119. These feeds of data 110, 111, 112, 113, 114, 115, may be periodic, sporadic, or continuous feeds. In an alternate embodiment of the invention, a clinical system interface that performs the functionality of the Clinical System Interface Engine 108 may be implemented as a part of one of the clinical modules. Thus, a clinical module, in such case, can send and receive data directly to and from the Expert System 119. One example of this is shown in FIG. 1 where the UI 116 of the Electronic Medical Record 107 is connected directly to the Expert System Interface Engine 125.

An Expert System 119 exists as a separate system from the Clinical System 101. The Expert System 119 may include an Expert System User Interface (ESUI) 123, an Expert System Database (ESDB) 124 and an Expert System Interface Engine (ESIE) 125 interconnected by various data feeds 120, 121, 122. The Expert System 119 is connected to the Clinical System 101 through the Clinical System Interface Engine 108 using various inbound and outbound data interfaces or feeds 130, 131, 132, 133, 134, 135, 136. The data interfaces or feeds have specific formats and data structures that define how and what data can pass through the data interface or feed. For instance, and not by way of limitation, the data passing through the interface or along the data feed may have specific headers, specific patient information elements, alert elements, order elements, and the like. These data interfaces or feeds will be discussed in individual detail below.

These various interfaces enable communication between an Expert System and a Clinical System, and/or the clinical modules associated with the Clinical System. These interfaces provide a structured manner by which data is bi-directionally communicated between the Clinical System, and the associated clinical modules, and the Expert System. Following hereinafter is a discussion of the exemplary interfaces associated with a Clinical System Interface Engine and an Expert System Interface Engine. In one embodiment, the interfaces may utilize industry standard message definitions, with such definitions being added to and modified to create the interface definitions described herein. Other embodiments of the invention allow for the use of proprietary message definitions. Proprietary message definitions, as well as industry standard definitions, can be used to ensure agreement in structuring messages transferred between an Expert System and a Clinical System.

As shown in FIG. 1, the Clinical System Interface Engine 108 and the Expert System Interface Engine 125 can communicate via an Inbound Data Interface (IDI) 133. This interface provides a conduit and message structure for transferring data regarding individual patients where that data has been input into the clinical modules of the Clinical System 101. These clinical modules can include, but are not limited to, Admission/Discharge/Transfer (ADT), laboratory (Lab) systems, pharmacy systems, orders systems, radiology systems, clinical documentation systems, clinical repositories, and other interface engines.

The following tables include illustrative data elements for specific Inbound Data Interface types. The following is only exemplary and other data elements may be used within the scope of embodiments of the present invention. Some embodiments implementing industry standard message definitions may include additional definitions, such as Z or other HL7 defined segments, which can be added for any interface transaction type.

TABLE 1

ADT segments

| | |
|---|---|
| MSH | Message Header |
| EVN | Event |
| PID | Patient Information |
| MRG | Merge |
| [{NK1}] | Next of Kin |
| PV1 | Patient Visit |
| [PV2] | Additional Patient Visit |
| [{DG1}] | Diagnosis |
| [{GT1}] | Guarantor |
| [{IN1}] | Insurance |
| [ACC] | Accident |

TABLE 2

Lab Segments

| | |
|---|---|
| MSH | Message Header |
| PID | Patient Information |

TABLE 2-continued

Lab Segments

| | |
|---|---|
| {[NTE]} | Comment |
| [PV1] | Patient Visit |
| [ORC] | Common Order |
| OBR | Order Detail |
| {[NTE]} | Comment |
| {[OBX]} | Observations/Results |
| {[NTE]} | Comment |

TABLE 3

Pharmacy Segments

| | |
|---|---|
| MSH | Message Header |
| PID | Patient Information |
| PV1 | Patient Visit |
| ORC | Common Order Information |
| RXR | Pharmacy Route |
| {RXE} | Pharmacy Encoded Order |
| [AL1] | Allergy information |
| [{OBX}] | Patient Height/Weight |

TABLE 4

Radiology Segments

| | |
|---|---|
| MSH | Message Header |
| PID | Patient Identification |
| PV1 | Patient Visit |
| ORC | Order Common |
| OBR | Observations Report ID |
| {[NTE]} | Notes and Comments |
| {[OBX]} | Observation/Results |

TABLE 5

Blood Gas (ABG) Segments

| | |
|---|---|
| MSH | Message Header |
| PID | Patient Information |
| ORC | Common Order Information |
| OBR | Observations Report ID |
| {[OBX]} | Observations/Results |

TABLE 6

Text (transcription) Segments

| | |
|---|---|
| MSH | Message Header |
| PID | Patient Identification |
| PV1 | Patient Visit |
| OBR | Observation Request |
| {[OBX]} | Observation/Result |

FIG. 1 illustrates the Expert System Interface Engine 125 sending messages on the Outbound Alert Interface 131 to the Clinical System Interface Engine 108. An Outbound Alert Interface provides a conduit and message structure for transferring alert information for specific patients from an alert generated by an Expert System. Asynchronous alerts generated within the Expert System can be sent in a message to an external Clinical System. This can be displayed in the external system's user messaging application. The external system can provide a mechanism to link to the Expert System and access the alert content directly. The content of the message may include one or more of the following:

1. Target user identifiers. The Expert System may identify a specific user who is the target of the alert.
2. Patient identifiers.
3. Alert session identifier.
4. Date/time stamp.
5. Alert identifier or name.
6. Alert message. This message can contain the reason the alert fired and a recommendation to use the Expert System to act on the alert.
7. Some identifier which the external system can use in a link utilizing the Inbound Application Interface to present the appropriate alert to a user directly when the Expert System is entered through the external application.
8. Urgency indicator. This indicated the urgency of the alert to the external system.
9. Update indicator. Sent concerning a previous alert, capable of updating the alert in the external system or of indicating the alert can be removed.

FIG. 1 illustrates the Expert System Interface Engine 125 sending messages to the Clinical System Interface Engine 108 on the Outbound Orders Interface (OOI) 135. An Outbound Orders Interface provides a conduit and message structure for transferring orders for a specific patient from an Expert System to a Clinical System. This interface can carry medication orders to an external system such as a pharmacy inpatient, pharmacy retail, or order management system. It may also carry orders for laboratory studies, radiology studies, or other clinical orders to be directed to the appropriate system. The orders may be sent to an order scratchpad, or equivalent area, of the external system so that the order can be processed from there. Alternatively, such orders may be sent directly to a pharmacy or other departmental system.

Both patient and user context may be passed by the OOI. This interface can carry order details. User comments, reject reasons, and related information are sent via the Audit Action Interface (described in more detail below). The content of the message may include one or more of the following:

1. User identifiers.
2. Patient identifiers.
3. Alert session identifiers.
4. Date/time stamp.
5. Alert identifier.
6. A list of orders and order actions. The reply can support one or more different orders.
7. Order details for each order in the list. This can use, for example, proprietary message definitions or industry standard message definitions such as the HL7 order interface standard.
8. Supported actions can include new orders, discontinue, hold/suspend, modify, and any other actions defined in the proprietary message definitions or industry standard message definitions.
9. Order identifier. This is an identifier from the external system that identifies a specific order instance in that system. It is needed to discontinue, modify, or take any other action on an existing order in the external system.

FIG. 1 illustrates the Expert System Interface Engine 125 sending messages to the Clinical System Interface Engine 108 on the Outbound Data Interface 134. An Outbound Data Interface provides a conduit and message structure for transferring data entered into the Expert System by a user or generated within the Expert System to the external system. This may be discrete, structured elements such as height or vital signs, or a document such as physician exam components, completed online rounds report, or a decision-supported progress note. For example, when the HL7 specifications are used, there can be one interface with separate HL7 OBX segments for data elements and for a document itself Patient and user context may be passed. The content of the message can include:

1. A proprietary message or industry standard message such as an HL7 OBR message, sent as, for example, an XML document. It may be implemented with the same elements as in the inbound data interfaces. This message may contain the identifiers for the data elements sent as well as the values for these elements. These elements may include for example, patient, date, time, nature of the data element, and origin.
2. Alert identifiers.
3. Alert session identifiers.
4. A proprietary message or industry standard message such as an HL7 allergy message may be used to send allergy information.
5. A proprietary message or industry standard message such as an HL7 diagnosis message may be used to send problem or diagnosis information.

FIG. 1 illustrates the Expert System Interface Engine 125 receiving messages from the Clinical System Interface Engine 108 on the Inbound Application Interface 132. An Inbound Application Interface provides a conduit and message structure for providing access to an Expert System from a link within an external system such as a Clinical System. The link determines the component of the Expert System that is accessed. The interface can contain all data needed by the Expert System, such as a drug or result that is in question. Patient and user context are maintained. If the link is present in the external system because of an alert generated in the Expert System, the interface message can contain an identifier to connect to that alert content in the Expert System. The contents of the message may include for example:

1. User identifiers.
2. Patient identifiers if present.
3. Alert session identifiers if relevant.
4. Date/time stamp.
5. Indicator of what part of the expert system to open.
6. Context for the link. If it is in a medication order, the message can contain the medication and associated order details. The message can also contain any patient information not expected to already be in the expert system.
7. Drug information, including drug, dose, route, frequency, duration, etc.
8. Lab information including lab tests, result value, interval of testing, etc.

FIG. 1 illustrates the Expert System Interface Engine 125 sending and receiving messages to and from the Clinical System Interface Engine 108 on the Synchronous Alert Interface 130. A Synchronous Alert Interface provides a conduit and message structure for supporting a synchronous interaction between an external system and an Expert System. Specifically, a Synchronous Alert Interface provides a message structure or protocol that allows an external system to request processing of orders or other clinical data by an Expert System so as to utilize features of the Expert System such as an alert generator. In this way, an Expert System can be used to analyze an order that is placed in the external order management system, such as a Computerized Physician Order Entry (CPOE) system, or a pharmacy system. The external system can call the Expert System with a message containing the order(s) to be analyzed, and can hold further processing of the orders pending the Expert System reply. The Expert System reply can identify whether or not an alert has fired. If an alert has fired, the reply can contain sufficient information to let the External System process the alert. This may involve automatically making changes, or it may require the external system to present the alert information to the user. The user can then determine whether or not to accept the recommendations. Once this occurs, the external system can communicate the outcome back to the Expert System for audit.

The Synchronous Alert Interface is a bi-directional interface. The expert system inbound interface of the Synchronous Alert Interface is from external system applications such as CPOE or a pharmacy order entry system. This is a request for processing by the Expert System alert engine. It contains patient and user context, as well as the specifics of the action being critiqued or analyzed. Because the present invention utilizes an interactive session between the Expert System and a Clinical System, it is desirable for the Expert System to have high performance.

The present invention supports synchronous interaction or communication between the Expert System and the Clinical System. Actions taken in the Clinical System are verified or analyzed in the Expert System and a response given by the Expert System to the Clinical System regarding the verification or analysis before the actions are completed or performed in the Clinical System. The reverse is also possible.

The Expert System outbound interface of the Synchronous Alert Interface contains the results of alert processing. If an alert is generated, then the alert contents with patient and user context are returned. If no alert is generated, then the reply so indicates. Audit information passes to a host system via the Audit Action Interface. This audit information transmission could be asynchronous.

The Expert System's processing of the present invention can be done without user interaction, and the reply is direct to the external system. The external system determines whether to launch the Expert System application directly or present the user with a link to the Expert System that allows the user to consult the Expert System. The external system may present information from the Expert System's reply within the external application, and allow user to accept or reject this information. If this implementation is chosen, audit information can be returned to the Expert System via the Audit Action Interface. The contents of the inbound message associated with Synchronous Alert Interface may include one or more of the following:

1. User identifiers.
2. Patient identifiers.
3. Alert session identifiers.
4. Date/time stamp.
5. List of orders with accompanying order details including order identifier, ordering physician.
6. Other clinical information relevant to the order such as lab results or allergy information.

The contents of the outbound message Synchronous Alert Interface can include one or more of the following:

1. User identifiers.
2. Patient identifiers.
3. Alert session identifiers.
4. Date/time stamp.
5. Alert flag to indicate whether an alert was generated.
6. List of additional orders with details.
7. List of orders to delete or change with details of changes.
8. An identifier the external system can use to allow the user to link directly to the Expert System alert in the Expert System if they want to interact with the Expert System to investigate and act upon the recommendation.
9. The message can be structured to carry multiple alerts triggered from one session.

FIG. 1 illustrates the Expert System Interface Engine 125 sending and receiving messages to and from the Clinical System Interface Engine 108 on the Audit Action Interface 136. Specifically, an Audit Action Interface provides a message structure or protocol that allows an external system and an Expert System to keep their alert audit trails synchronized. The external messaging system may allow a user to dismiss an alert directly, and the Expert System needs to close out the audit trail on that alert. Alternatively, an external alert audit mechanism may be updated to reflect the actions users take within the Expert System. This also provides the external system a mechanism to present the outcome of an alert at later points in the patient care process when the issue arises again.

The Expert System inbound audit message contains action and override reasons when an alert presented in an external system is acted upon by user. This allows the Expert System to update its audit log when an alert is dismissed from within external system.

The Expert System outbound audit message contains action and override reasons when alert is acted upon within the Expert System, and allows the external system to maintain its audit trail.

The Expert System outbound audit message also allows external systems to display override reasons and other comments to additional users when the alert content is displayed to them. For example, if a pharmacist subsequently views a physician comments on an alert, the pharmacist can also view the physician's actions and stated rationale.

Override reasons can be codified to allow efficient search and standardization of reasons where possible. However, the message structure can also support free text comments.

The interface is bi-directional, but the content of messages is the same in both directions. The contents of the message can include:

1. User identifiers.
2. Patient identifiers.
3. Alert session identifiers.
4. Date/time stamp.
5. Alert identifier.
6. Alert action.
7. Codified override reason.
8. User comments.

Generally, the Expert System of the present invention contains a knowledge base and a means or mechanism for holding patient information, such as hardware and/or software modules and components. The Expert System can include an interface engine that receives data into the Expert System and transmits it back into one or more external clinical systems that can communicate with the Expert System using one or more interfaces. The Expert System can also include an inference engine that pre-processes the incoming data, and one or more knowledge engines that apply knowledge from the knowledge base to individual and population patient information.

The Expert System can interface with one or more Clinical Systems or other systems. For instance, the Expert System may interface with a Clinical Data Repository, an individual data system, such as a lab or pharmacy, an interface engine, or other repositories, systems, or engines.

Generally, as used herein, Expert System may not refer to the entire broad category of expert systems, such as those used in artificial intelligence applications. Rather while the Expert Systems described herein may incorporate principles of artificial intelligence, an Expert System as used herein is a type of Clinical Decision Support System (CDSS) as that term is understood by those skilled in the art of medicine.

The Expert System 119 and the Clinical System 101 may, in some embodiments, comprise one or more special purpose and/or one or more general purpose computers including various computer hardware components. Aspects of the invention also may be described in terms of methods comprising functional steps and/or non-functional acts. The following is a description of acts and steps that may be performed in practicing the present invention. Usually, functional steps describe the invention in terms of results that are accomplished, whereas non-functional acts describe more specific actions for achieving a particular result. Although the functional steps and non-functional acts may be described or claimed in a particular order, the present invention is not necessarily limited to any particular ordering or combination of acts and/or steps.

The invention will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

In addition to the above, embodiments of the present invention may also include computer-readable media for carrying or having the computer-executable instructions or data structures stored thereon, such instructions of data structures may be computer software code. Such computer-readable media can be any available media that can be accessed by a general purpose or special purpose computer. By way of example, and not limitation, such computer-readable media can include RAM, ROM, EEPROM, CD-ROM or other optical disc storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions include, for example, instructions and data which cause a general purpose computer, special purpose computer, or special purpose processing device to perform a certain function or group of functions.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices. These computer systems may include various interfaces including keyboards, mice, computer monitors, network connections, and the like.

As mentioned above, portions of the Clinical System 101 may be implemented as computer software code on one or more computer systems. The software code of the Clinical System 101 is a separate application with respect to the software code of the Expert System 119. However, those of skill in the art will appreciate that, although separate applications, the Expert System 119 and the Clinical System 101 may be running on a common computer system or network of computer systems. Further, while the Expert System 119 and the Clinical System 101 are separate systems, embodiments of the invention include interfaces such as the Expert System Interface Engine 125 for facilitating standardized communications between the Expert System 119 and the Clinical System 101. While the Expert System Interface Engine 125 is shown as a separate module of the Expert System 119, it should be understood that an Exert System Interface may be implemented at any appropriate location. For example, an Expert System Interface may be implemented as part of the Expert System Database 124 or at any other suitable location. The Expert System Interface still includes the functionality of the Expert System Interface Engine 125 as described herein. Similarly, other modules within the Expert System 119 and Clinical System 101 can be implemented in other locations, within those systems respectively, than those shown in the exemplary drawings while still being within the scope of embodiments of the present invention.

Figure 2:
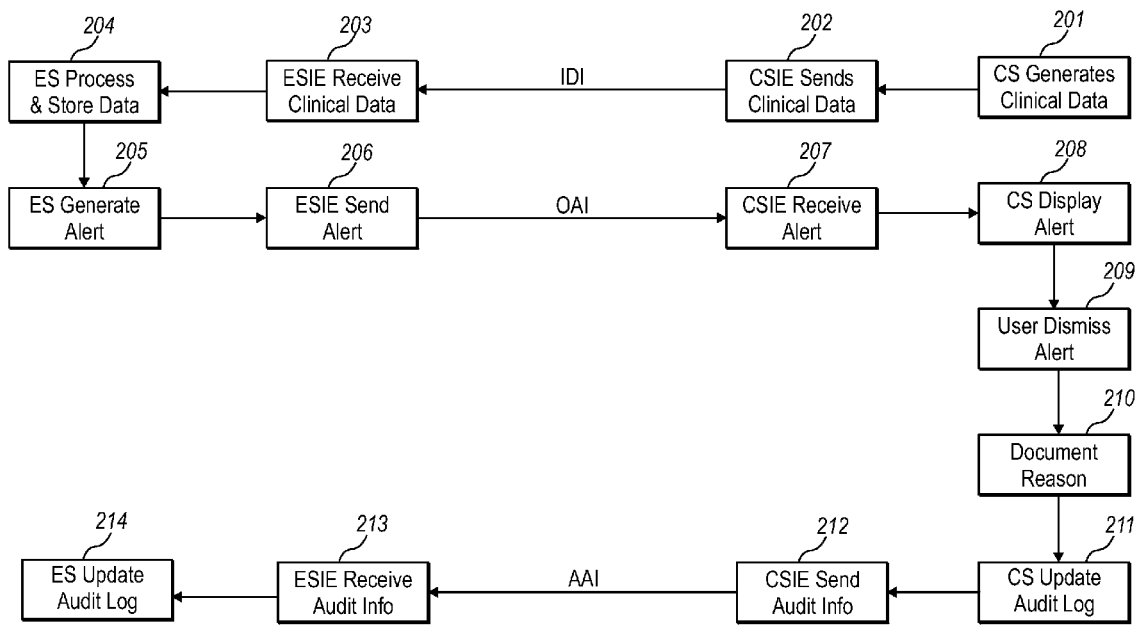
FIG. 2 illustrates a workflow diagram illustrating a use of the system shown in FIG. 1.

One exemplary workflow associated with the system of FIG. 1 is illustrated in FIG. 2. With continuing reference to FIGS. 1 and 2, the Clinical System 101 generates clinical data "box 201". Clinical data may be generated by a physician entering data into the Clinical System 101 or one of its modules 130-136 through UI 116. The data can also be obtained from test results, admission and discharge data entered by a hospital admitting department, ordering or providing medications, and the like. The clinical data may be sent by the Clinical System Interface Engine 108 across the Inbound Data Interface 133 "box 202". The Expert System Interface Engine 125 receives the data from the Inbound Data Interface 133 "box 203", and processes it. This processing may include attaching a standard data identifier to data elements in the message, followed by processing by the Expert System Interface Engine 125 within the Expert System 119. The processed information may then be stored within the Expert System Database 124 for further processing "box 204". The further processing may be accomplished, for example by a clinical decision module 126. In this example, the clinical decision module is shown as software code that is part of the Expert System Database 124. However, the decision module 126 may be implemented in other locations within the Expert System 119. The clinical decision module 126 can include an inference engine that uses the expert data, i.e., data representative of knowledge in the medical field relating to the diagnosis and treatment of medical conditions stored in the Expert System Database 124, to determine treatment options for a particular patient based upon the data received from Clinical System 101.

On occasion, the Expert System 119 can also generate an alert "box 205". This alert may be specific to a patient, and related to some aspect of clinical care such that the user at any one or all of the UI 116 could be notified, for instance, to take an action or with information or data associated with patient. This alert can be sent from the Expert System 119 via the Expert System Interface Engine 125 to the Clinical System 101 via the Outbound Alert Interface 131 "box 206". This message can be pushed from the Expert System 119 to the Clinical System 101, or it can be requested or queried by the Clinical System 101. The Clinical System 101 receives the alert "box 207" and displays the alert "box 208" through one or more of a variety of display mechanisms, such as one of the UI 116, associated with the Clinical System 101. This could include display of an alert message in an inbox or other messaging system within the electronic medical record 107. Alerts may also be transmitted to pagers, email inboxes, voice messaging services, and the like of a patient's physician or some other individual. Illustratively, the alert may be displayed in association with a record related to the patient. This record may be any record within the Clinical System 101. For instance, the record could be, by way of example, a patient's laboratory record, radiology record, pharmacy record, CDR record, ADT record, etc. A user is able to view this alert, and determine whether to take any action.

With continued attention to FIG. 2, if the user determines that they do not want to take any action on the alert, they may dismiss the alert "box 209". Doing so may require the user to provide a reason for dismissal, which is documented into the Clinical System 101 "box 210". The Clinical System 101 updates its audit log appropriately "box 211". When the alert is dismissed, the Clinical System 101 also sends an audit information message to the Expert System 119 via the Audit Action Interface 136 "box 212". The audit information message is received by the Expert System Interface Engine 125 "box 213". The audit information message contains information to allow the Expert System 119 to update its audit log as well "box 214".

Figure 3:
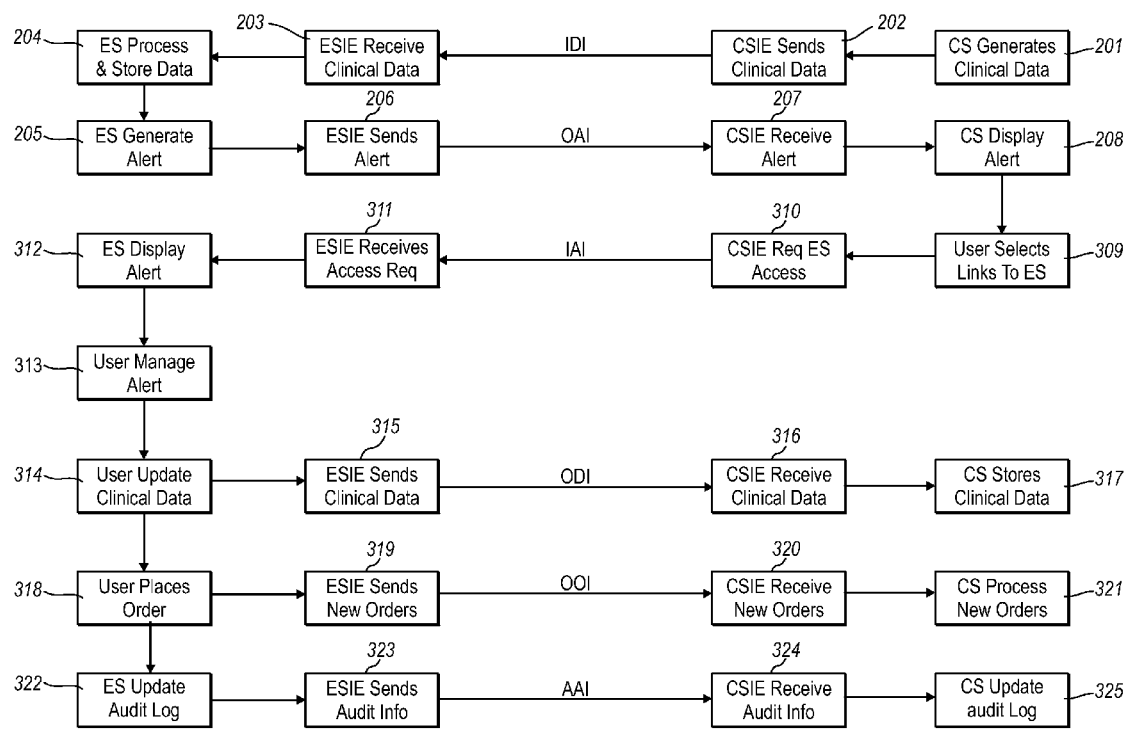
FIG. 3 illustrates a workflow diagram of an alternative use of the system shown in FIG. 1.

When the user determines that they wish to take further actions on the alert, the workflow illustrated in FIG. 3 may be followed. FIG. 3 includes boxes 201 through 208 which represent the same actions and functions performed and shown with those designations in FIG. 2. The following description describes, in conjunction with FIG. 3, actions and functions performed when a user decides to take further actions on an alert as opposed to simply dismissing the alert as was illustrated in FIG. 2. With reference to FIGS. 1 and 3, the user is allowed to access the Expert System 119 by selecting a link or similar mechanism within the user interface UI 116 of the Clinical System 101 "box 309". For example, the Clinical System 101 may provide a user interface 116 that includes links such as hyperlinks, buttons, radio buttons, pull-down menus, lists and the like. A link such as one of these may be tied to the Expert System 119. Selecting this link provides the user access to the alert within the Expert System 119. Namely, the Clinical System Interface Engine 108 requests access from the Expert System 119 (box 310). The request is sent via the Inbound Application Interface 132 and received by the Expert System Interface Engine 125 "box 311". The request contains information to allow the Expert System 119 to display the data associated to the correct alert "box 312", while maintaining patient and user context provided by the Clinical System 101. For instance, the same frame of a User Interface 116 can contain data that is stored at the Clinical System 101 and data received from the Expert System 119. Alternatively, selecting the link can initiate a "pop-up" window within the application opening at the Clinical System 101 that contains the data associated with the alert.

In either case, the user is now able to work within the Expert System 119, through one of the UI 116 at the Clinical System 101 to manage the alert "box 313". Managing the alert, may include the user updating clinical data "box 314". The user may wish to enter additional patient information that is needed to complete processing or managing the alert. As a result of processing or managing the alert, the Expert System 119 itself may also generate patient information or inferences concerning the patient. If this information is clinical information that can be stored in the clinical systems, such as height, weight, diagnosis, or other clinical data, the Expert System Interface Engine 125 can send this clinical data "box 315" such that is received by the Clinical System Interface Engine 108 "box 316" via the Outbound Data Interface 134. The Clinical System 101 can then process and store "box 317" this new clinical data according to its design.

As an outcome of the alert and processing and managing the alert, the user may wish to place orders "box 318" to be applied to the patient. These orders may include diagnostic studies or testing, or adding, modifying, or discontinuing medication or other orders. Any new orders can be sent using the Expert System Interface Engine 125 "box 318" to the external Clinical System 101 "box 320" using the Outbound Orders Interface (OOI) 135. The Clinical System (CS) 101 then processes the new orders "box 321" by the Clinical System Interface Engine 108 delivering the new order(s) to the clinical module(s) that are to receive such order(s).

Upon completion of managing and processing the alert, the outcome of the alert and any actions taken by the Clinical System 101 can be updated in the Expert System 119 and its audit log "box 322". Following updating, an audit info message is sent to the Clinical System 101 "box 323" via the Audit Action Interface 136. This audit info message can contain a log of actions taken and any reasons the user of the Clinical System 101 has entered for these actions. When the audit info message is received by the Clinical System Interface Engine 108 "box 324", the Clinical System 101 can updates its own audit logs appropriately "box 325". The user can be returned to the Clinical System 101 from the Expert System 119.

Figure 4:
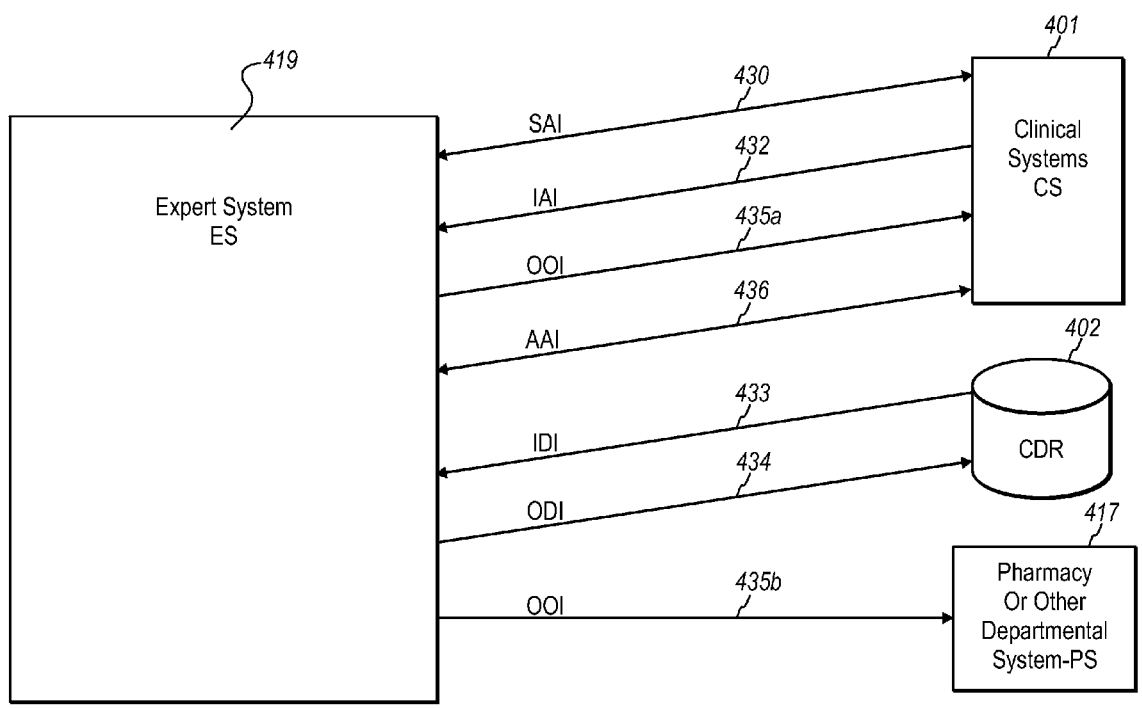
FIG. 4 illustrates a schematic diagram of another exemplary embodiment of the present invention, representing another model of interface implementation between a clinical system and an expert system.

Another exemplary embodiment of the present invention is shown in schematic form in FIG. 4. The embodiment shown in FIG. 4 illustrates an Expert System 419 coupled to a Clinical System 401, and other clinical modules including a Clinical Data Repository 402 and a pharmacy system 417. Alternatively, the pharmacy system 417 may be some other suitable departmental system. Notably, as used herein, a clinical system may refer to a collection of clinical modules. A clinical system may also refer to a collection of smaller clinical systems, or any combination of smaller clinical systems and clinical modules. Those skilled in the art understand that the clinical modules shown herein are often referred to as clinical systems. The term clinical modules is used to illustrate a separate nature of smaller clinical systems within a collection of clinical systems, or to illustrate a separate nature of smaller clinical systems from other clinical systems. Thus, a clinical system may actually be comprised of other clinical systems. The Expert System 419 is connected to the Clinical System 401, Clinical Data Repository 402 and pharmacy 417 systems via data feeds 430, 432, 433, 434, 435*a*, 435*b* 436, similar to the data feeds 130, 132, 133, 134, 135 136 shown in FIG. 1.

Figure 5:
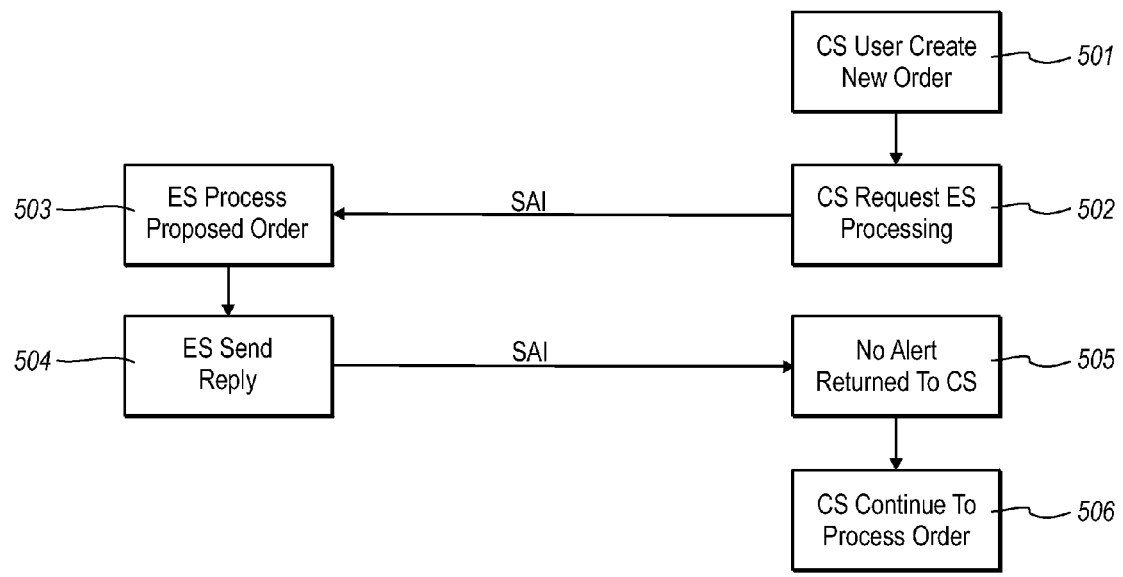
FIG. 5 illustrates a workflow diagram illustrating a use of the system shown in FIG. 4.
Figure 6:
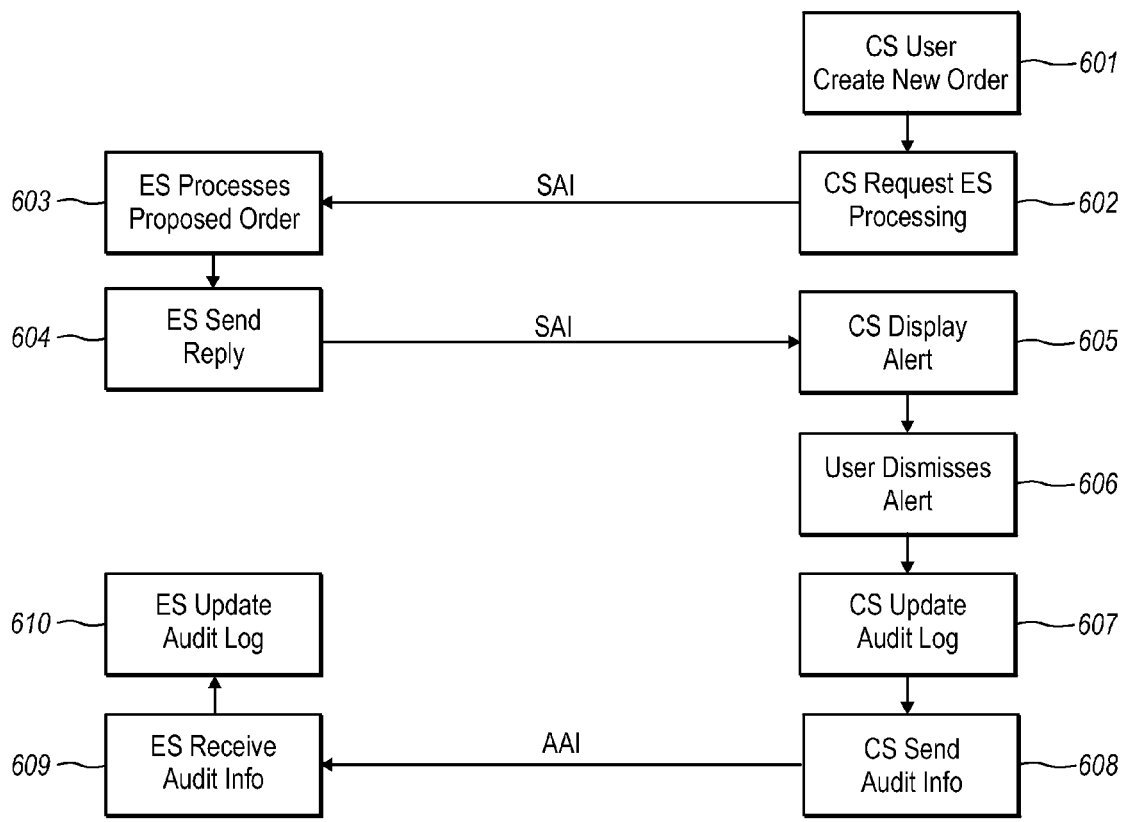
FIG. 6 illustrates a workflow diagram illustrating another alternative use of the system shown in FIG. 4.
Figure 7:
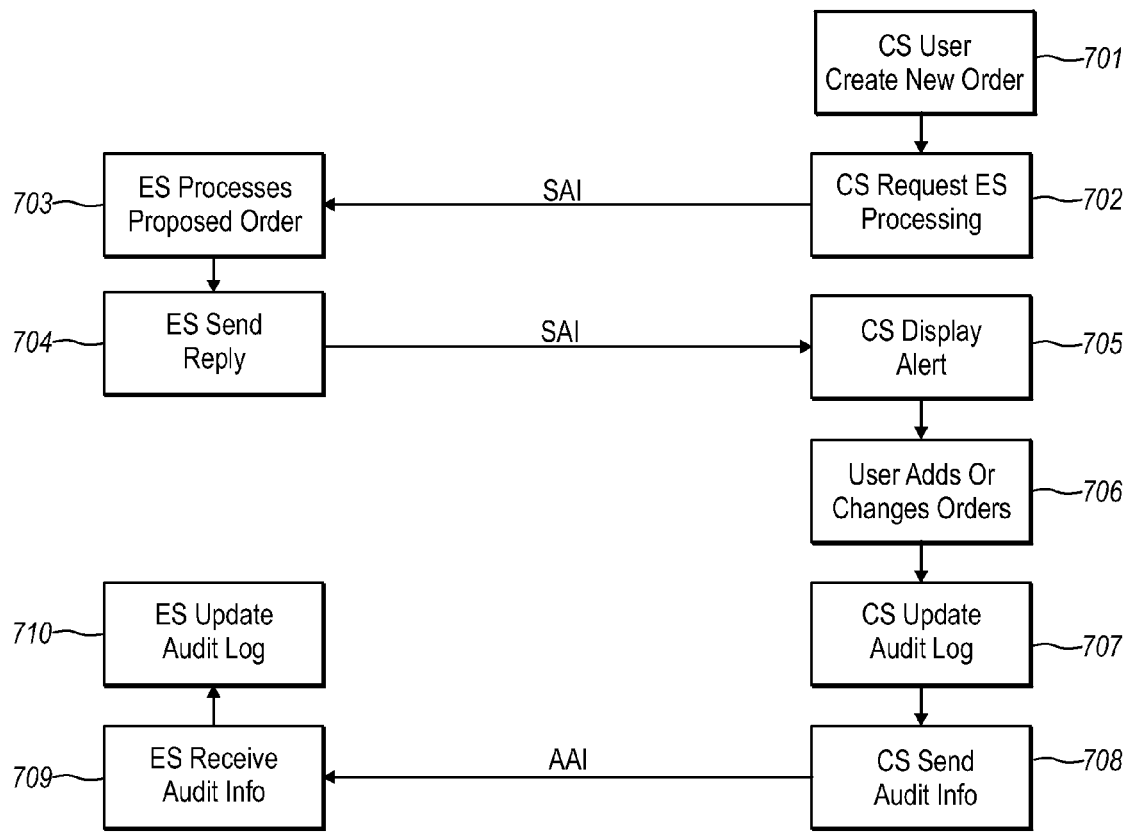
FIG. 7 illustrates a workflow diagram illustrating yet another alternative use of the system shown in FIG. 4.

Three exemplary workflows within this embodiment are illustrated in FIGS. 5, 6, and 7. With attention now directed to FIGS. 4 and 5, in FIG. 5, a clinician can use a Clinical System 401 to create or modify orders for a patient "box 501". The Clinical System 401 can generate a request for processing by the Expert System 419 (box 502). The new order, as described above in the interface description, can be sent to the Expert System 419 via the Synchronous Alert Interface 430. The message sent on the Synchronous Alert Interface 430 may contain user and patient identifiers, as well as the new order and other order details such as dose, route, frequency, and duration. The message may also contain other details to aid in evaluating the order within the Expert System 419. The new order message is sent synchronously, meaning that further processing of the order within the Clinical System 401 is halted until a reply is received from the Expert System 419. Upon receipt of this message, the Expert System 419 can immediately process the contents of the message "box 503", and send its reply "box 504" back to the Clinical System 401 via the Synchronous Alert Interface 430. This reply message can contain an indication of whether an alert was generated. If no alert was generated "box 505", the Clinical System 401 can continue its processing "box 506" by sending the order request to the appropriate clinical module.

With attention now directed to FIGS. 4, 6, and 7, again, a clinician uses a Clinical System 401 to create or modify orders for a patient "boxes 601, 701". The Clinical System 401 requests the Expert System 419 to process the orders "boxes 602, 702". The Expert System 419 processes the proposed order "boxes 603, 703", as described above. In these examples, an alert is generated. The reply from the Expert System 419 "boxes 604, 704" can contain information about the nature of the alert, Similar to other alerts generated by the Expert Systems 419 of the present invention. It may contain specific patient and user information, as well as a detailed recommendation, such as, but not limited to, a suggestion to discontinue an order or to place an order for a specific medication. The reply may contain any or all of the details to generate the order in the Clinical System 401. The reply may also contain link information, such a link address that can be displayed to and accessible by the clinician, physician, or other individual through user interface (such as the UI 116 FIG. 1) on the Clinical System 401. This link enables the user to access the Expert System 419 directly from the Clinical System 401 by initiating a call through the Inbound Application Interface 432. The Clinical System 401 displays the alert to the user "boxes 605, 705", such as by displaying a message in a user interface UI 116 on the Clinical System 401, to allow the user to act upon it.

Continuing the illustrative process, in FIG. 6, the user may determine that the alert is not appropriate, or otherwise decide to dismiss the alert "box 606". The Clinical System 401 provides a resource to dismiss the alert and to capture any reason given by the user for dismissing the alert. For instance, the Clinical System 401 may present a user interface that includes a link or button through which a user may dismiss the alert and a textbox to provide reasons for such dismissal. This information associated with the dismissal of the alert may be used to update the audit log of the Clinical System 401 "box 607". In addition, the Clinical System 401 can send a message containing audit information to the Expert System 419 via the Audit Action Interface 436 "box 608". This permits the Expert System 419 to receive the audit information "box 609" and to update its audit log appropriately "box 610".

Alternatively to the process described in FIG. 6, the user may determine that the alert is appropriate, and decide to take one or more recommended actions, as illustrated in FIG. 7. These actions may be generated within the Clinical System 401. In the example shown in FIG. 7, the user may add or change orders "box 706". These additions or changes can be made using the Expert Systems 419, the Clinical System 401, or the associated clinical modules. Upon completion of the taken actions, the Clinical System 401 updates its audit log "box 707". In addition, the Clinical System sends a message containing audit information detailing the actions taken to the Expert System 419 "box 708" via the Audit Action Interface 436 "box 708". This permits the Expert System 419 to receive the audit information "box 709" and to update its audit log appropriately "box 710".

Figure 8:
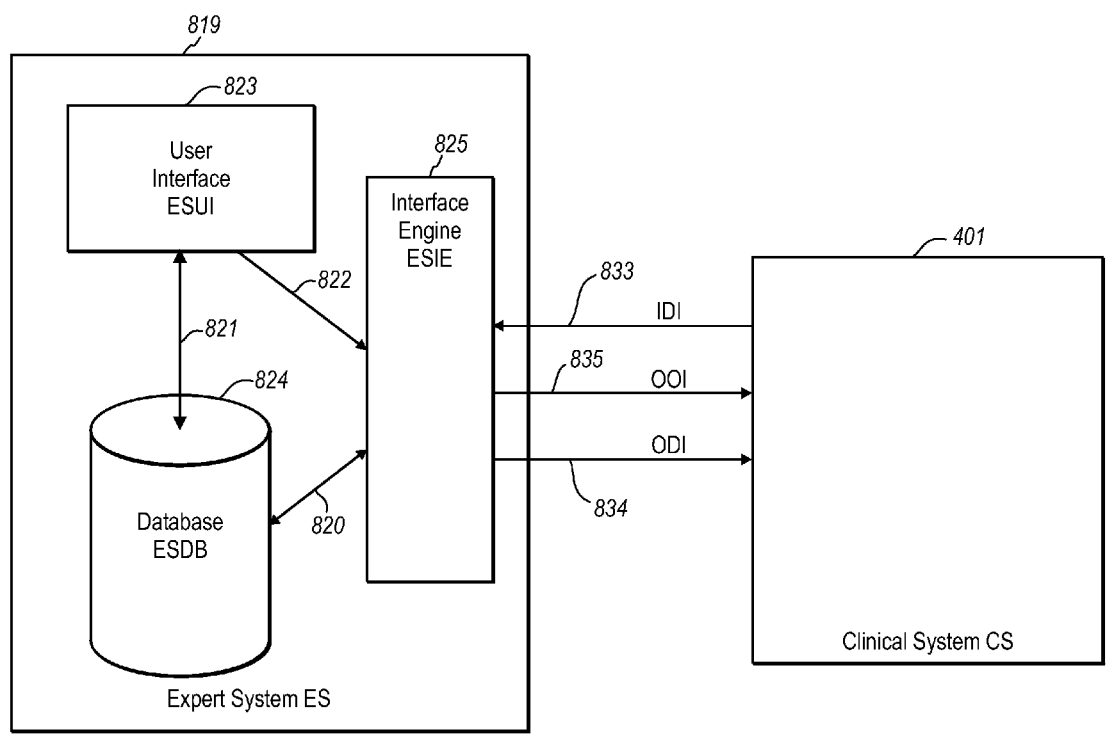
FIG. 8 illustrates a schematic diagram of another exemplary embodiment of the present invention, representing yet another model of interface implementation between a clinical system and an expert system.

Yet another exemplary embodiment is shown in schematic form in FIG. 8. FIG. 8 illustrates an Expert System 819 that includes an Expert System User Interface an Expert System Database 824 and an Expert System Interface Engine 825 interconnected by various data feeds 820, 821, 822 similar to the data feeds 120, 121 122 in FIG. 1.

Figure 9:
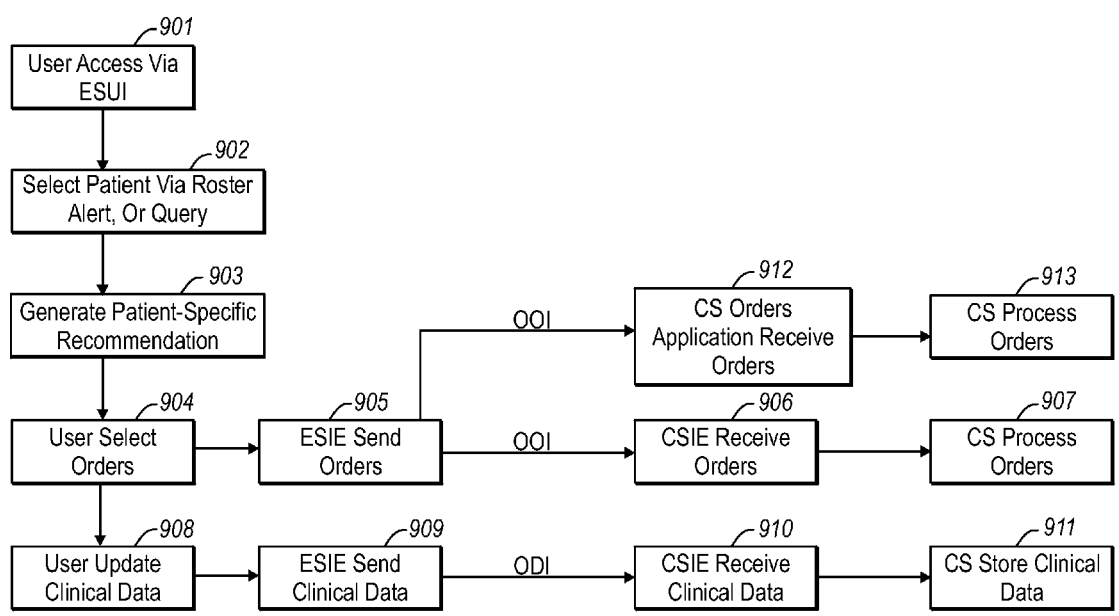
FIG. 9 illustrates a workflow diagram illustrating a use of the system shown in FIG. 8.
Figure 1:
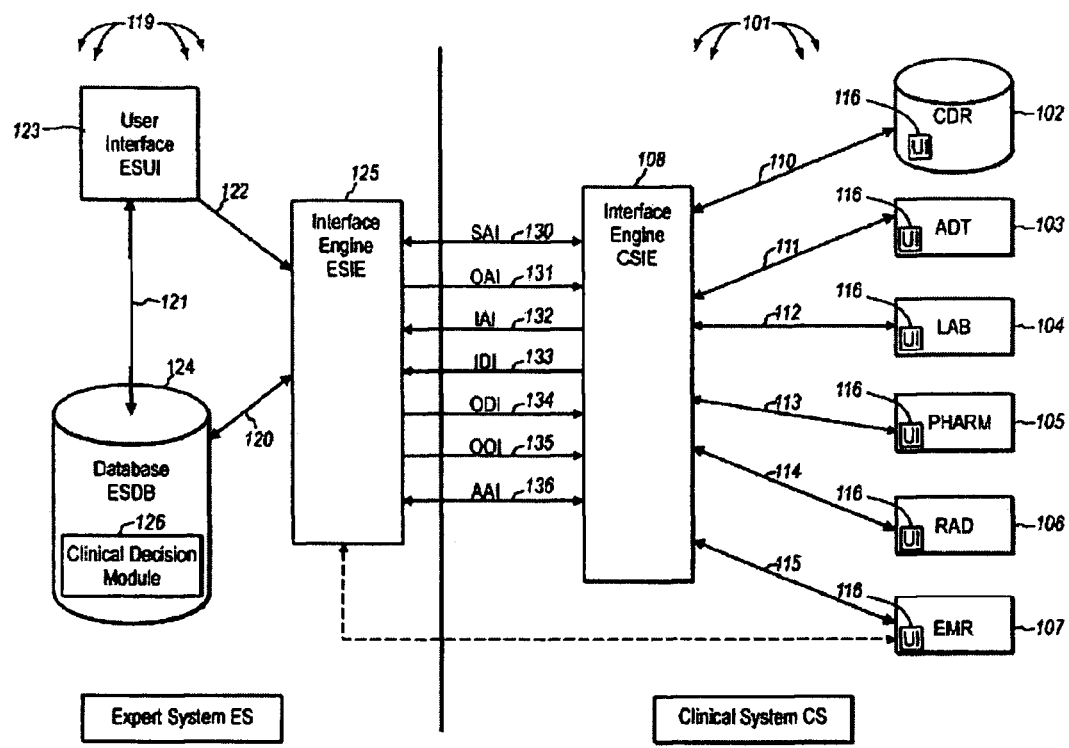
Figure 4:
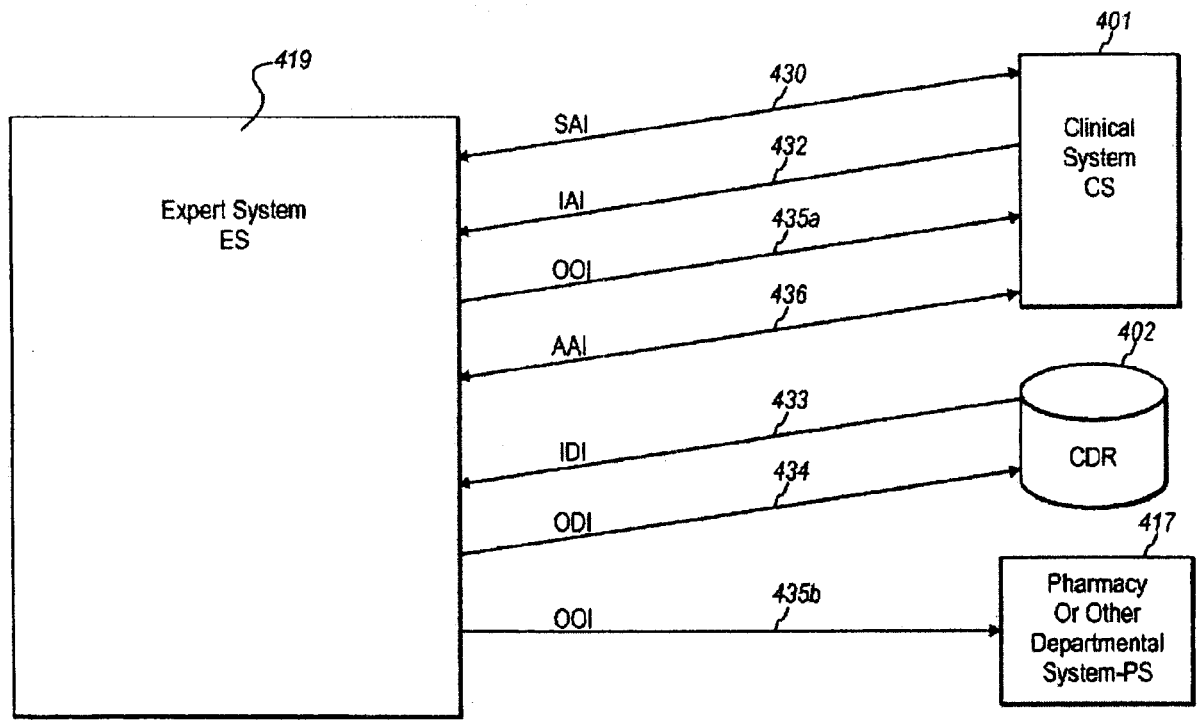
Figure 8:
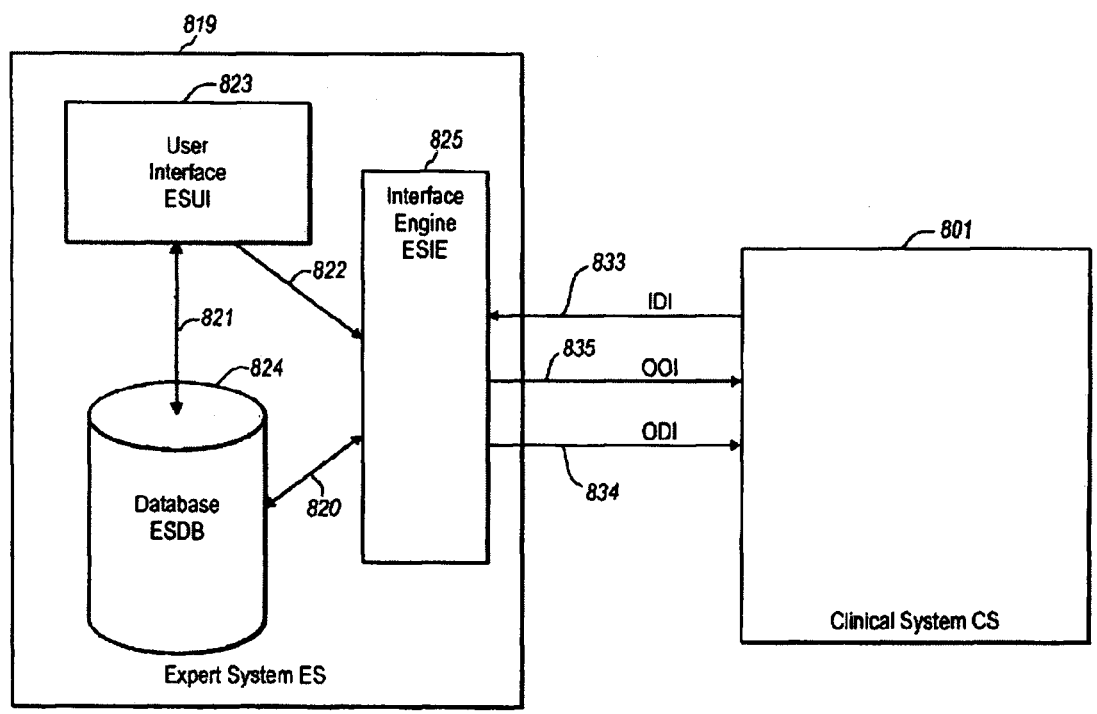

The Expert System 819 is connected via the Expert System Interface Engine 825 and various data feeds 833, 834, 835 similar to the data feeds 133, 134, 135 in FIG. 1 to a Clinical System 801. The Expert System 819 may be similar to other expert systems described herein such as the Expert System 119 in FIG. 1. A possible workflow for this embodiment is illustrated in FIG. 9. With attention now directed towards FIGS. 8 and 9, in this example, the user accesses the Expert System 819 directly via the Expert System User Interface 823 "box 901". Because the Inbound Data Interface 833 provides a feed of patient identification information and patient data, the user is able to select a specific patient within the Expert System 819 "box 902". Alternatively, the Expert System 819 may, through its processing, generate alerts which are presented within the Expert System User Interface 823. The user may access data specific to the selected patients through selecting these alerts. Alternatively, the user may query the Expert System 819 through its User Interface 823 for patients meeting specified criteria, and may then access specific patient identification information and data through the results of this query. The query returns a list of patients meeting the specified criteria. The user may then select patients from the returned list to access patient information. The query may be formulated in the User Interface 823, by using for example, menus, drop-down menus, data fields, text boxes and the like. In yet another alternative embodiment, the Expert System 819 may present the user with lists or rosters of patients, from which a specific patient may be identified so that information can be accessed through its User Interface 823. The rosters or lists may be lists based on patient location, clinical service, attending or consulting physician, or other patient lists maintained within the clinical system. They are displayed in the Expert System 819 such as by displaying in the User Interface 823. The user may select a patient from the roster or list. In yet another alternative embodiment, the Expert System 819 may present a patient-specific view of clinical information, such as a summary or rounds report for a given physician, clinician, clinic, department, etc. within its User Interface 823, through which a user may access data specific to the selected patient.

Once the user has accessed data associated with a specific patient, the user may then use the expert knowledge contained in the knowledge base of the Expert System 819 to generate patient-specific recommendations "box 903" for therapy or for further evaluation. The user is able to select specific orders "box 904" that are then sent to the Clinical System 801 "box 905" through the ESIE 825 via the Outbound Orders Interface 835. The Outbound Order Interface 835 may communicate with the Clinical System 801 via the Clinical System Interface Engine or directly with an orders application within the Clinical System 801. In the latter instance the Expert System Interface Engine 825 sends the orders across the Outbound Order Interface directly to the orders application, or some other clinical module, within the Clinical System 801 (box 905). The orders application then receives the orders "box 912" and may then complete any necessary processing of the order "box 913". The Clinical System 801 receives "box 906" and processes the orders "box 907". If the user entered clinical data for the patient that could be stored within the Clinical System 801 or the Expert System 819 generated such data from its processing, this may be sent to the Clinical System via the Outbound Data Interface.

An optional feature of an exemplary expert system is a mechanism to standardize data and vocabulary terms between the expert system and the clinical system. In one configuration, a Vocabulary Server is part of the Expert System. The vocabulary server includes modules or software that assigns a vocabulary term to a data element. In one embodiment of the invention, the identifiers for data elements within the Clinical System are initially mapped to standard nomenclatures. All data elements which are received from the Clinical System are stored with standard nomenclature identifiers attached within the Expert System database, based upon this mapping. For data elements which are not mapped initially, there may be functionality in the Vocabulary Server which allows the system to identify the best match to a standard nomenclature identifier. This allows a system to attach a standard identifier to each of one or more data elements that may have different identifiers based on their generation in their originating systems, but which in fact represent the same entity. In an exemplary embodiment, this Vocabulary Server is a component of the Expert System Interface Engine. As each inbound data element is received from the Clinical Systems, the Vocabulary Server attaches a standard identifier to the received data. As each outbound data element is written to a message to be sent out of the Expert System Interface Engine, the Vocabulary Server assigns the appropriate external identifier based on the standard identifier that is attached by utilizing the above mapping of Expert System nomenclature identifiers to the Clinical System data elements.

In another configuration, the Vocabulary Server is a component of the Clinical System Interface Engine. As each data element is sent to the Expert System Interface Engine, a standard identifier is applied. The reverse is performed on data sent to the Clinical System Interface Engine, as standard identifiers received are mapped to local identifiers.

In yet another configuration, the data standardization is a dynamic process within the Expert System. Data elements are stored as they are sent in through the interface. As the data elements are accessed by the Expert System, the Vocabulary Server maps each element to a standard identifier to be used in the Expert System processing.

In yet another configuration, the data elements in the Clinical Systems are all stored with standard identifiers, and these identifiers are sent through the interfaces. No additional mapping is performed by the interfaces, nor by the Expert System itself. In this instance, the use of data and vocabulary standards throughout both the Clinical System and the Expert System removes the need for a Vocabulary Server.

Vocabulary Servers may be implemented by custom design. However, Vocabulary Servers may also be implemented in embodiments of the invention by using a commercially available Vocabulary Server. Such servers are readily available from Health Language Inc. of Aurora, Colo. and Apelon Inc. of Ridgefield, Conn.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

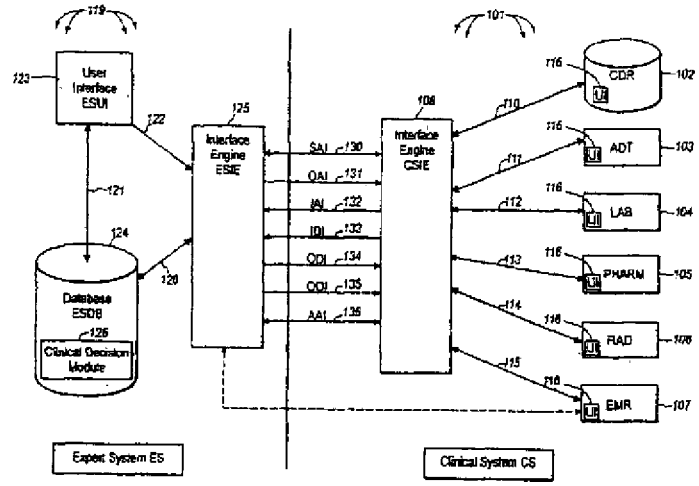

What is claimed is:

1. A computer program product for use in a system where a separate expert system is configured to communicate with a clinical system having one or more clinical modules, and notwithstanding that the separate expert system and the clinical system are configured to process data having different and otherwise incompatible data formats, the computer program product for implementing a method of interfacing the separate expert system with the clinical system, the computer program product comprising one or more physical storage media have stored thereon computer-executable instructions that, when executed at a processor, cause the system to perform the method, including the following:

receive clinical data from the clinical system on at least one of an inbound data interface and a synchronous alert interface, the clinical data having a first format structured for compatible processing at the clinical system;

modify the structure of the clinical data to a second different format structured for compatible processing at the separate expert system such that the clinical data can be compatibly processed at the separate expert system, wherein without the structural modification of the clinical data the separate expert system is unable to compatibly process the clinical data;

store the modified clinical data in an expert system database of the expert system in the second different format;

process the modified clinical data in the expert system to make a medical decision;

generate an alert based on results of processing the modified clinical data, the alert having the second different data format structured for compatible processing at the separate expert system;

modify the structure of the generated alert to the first format such that the generated alert can be compatible processed at the clinical system, wherein without the structural modification of the generated alert the clinical system is unable to compatibly process the alert; and send the modified generated alert to the clinical system on at least one of the synchronous alert interface and the outbound alert interface.

2. The computer program product of claim 1, further comprising computer-executable instructions that, when executed, cause the computer system to:

receive audit information on an audit action interface from the clinical system when the alert has been dismissed at the clinical system; and update an audit log in the expert system.

3. The computer program product of claim 1, further comprising computer-executable instructions that, when executed, cause the computer system to:

receive a request on at least one of a synchronous alert interface and an inbound application interface from the clinical system for access to the expert system;

display the alert from the expert system at the clinical system;

receive an update of clinical data on at least one of a synchronous alert interface, an inbound application interface and an inbound data interface from a user at the clinical system; and send the update of clinical data to the clinical system using at least one of the synchronous alert interface and the outbound data interface.

4. The computer program product of claim 3, further comprising computer-executable instructions that, when executed, cause the computer system to update an audit log at the expert system.

5. The computer program product of claim 3, further comprising computer-executable instructions that, when executed, cause the computer system to:

receive an order; and send the order to a clinical module.

6. The computer program product of claim 5, further comprising computer-executable instructions that, when executed, cause the computer system to update an audit log at the expert system.

7. The computer program product of claim 1, wherein computer-executable instructions that, when executed, cause the computer system to send the modified generated alert to the clinical system comprise computer-executable instructions that, when executed, cause the computer system to push the alert from the expert system.

8. The computer program product of claim 1, wherein computer-executable instructions that, when executed, cause the computer system to send the modified generated alert to the clinical system comprise computer-executable instructions that, when executed, cause the computer system to:
receive a request or query from the clinical system; and
send the alert to the clinical system in response to the request or query.

9. The computer program product of claim 1, wherein computer-executable instructions that, when executed, cause the computer system to generate an alert based on results of processing the modified clinical data comprise computer-executable instructions that, when executed, cause the computer system to generate an alert that comprises data elements and further comprising:
computer-executable instructions that, when executed, cause the computer system to attach standard identifiers to at least a portion of the data elements.

10. The computer program product of claim 1, further comprising computer-executable instructions that, when executed, cause the computer system to structure messages including the modified generated alert according to proprietary message definitions.

11. The computer program product of claim 1, further comprising computer-executable instructions that, when executed, cause the computer system to structure messages including the modified generated alert according to industry standard message definitions.

12. The computer program product of claim 11, wherein computer-executable instructions that, when executed, cause the computer system to structure messages including the modified generated alert according to industry standard message definitions comprise computer-executable instructions that, when executed, cause the computer system to structure messages including the modified generated alert according to the HL7 protocol.

13. The computer program product of claim 1, wherein computer-executable instructions that, when executed, cause the computer system to receive clinical data from the clinical system comprise computer-executable instructions that, when executed, cause the computer system to receive clinical data from an interface engine disposed on a clinical module within the clinical system.

14. A computer program product for use at an expert system separate from a clinical system and configured to communicate with the clinical system, the computer program product for implementing a method of providing clinical decision support, notwithstanding that the separate expert system and the clinical system are configured to process data having different and otherwise incompatible data formats, the computer program product comprising one or more physical storage media have stored thereon computer-executable instructions that, when executed at a processor, cause the system to perform the method, including the following:
receive an order on at least one of a synchronous alert interface and an inbound data interface, from the clinical system, the order having a first format structured for compatible processing at the clinical system;
modify the structure of the order to a second different format structured for compatible processing at the separate expert system such that the order can be compatibly processed at the separate expert system, wherein without the structural modification of the order the separate expert system is unable to compatibly process the order;
process the modified order to generate a response to the order, the response having the second different data format structured for compatible processing at the separate expert system;
modify the structure of the response to the first format such that the response can be compatible processed at the clinical system, wherein without the structural modification of the response the clinical system is unable to compatibly process the response; and
send the modified response to the clinical system on at least one of the synchronous alert interface, an outbound data interface and an outbound orders interface.

15. The computer program product of claim 14, wherein computer-executable instructions that, when executed, cause the computer system to process the modified order to generate a response to the order comprise computer-executable instructions that, when executed, cause the computer system to generate a response that is an alert, and further comprising computer-executable instructions that, when executed, cause the computer system to:
receive audit information from the clinical system on at least one of a inbound audit interface, inbound data interface, and an audit action alert interface when the alert has been dismissed at the clinical system; and
update an audit log in the expert system.

16. The computer program product of claim 14, wherein computer-executable instructions that, when executed, cause the computer system to process the modified order to generate a response to the order comprise computer-executable instructions that, when executed, cause the computer system to generate a response that is an alert, and further comprising computer-executable instructions that, when executed, cause the computer system to:
receive audit information from the clinical system on at least one of a inbound audit interface, inbound data interface and an audit action alert interface when the alert results in an addition or change to the orders at the clinical system; and
update an audit log in the expert system.

17. The computer program product of claim 14, wherein computer-executable instructions that, when executed, cause the computer system to receive an order comprise computer-executable instructions that, when executed, cause the computer system to receive and order that includes data elements, and further comprising computer-executable instructions that, when executed, cause the computer system to assign standard identifiers to at least a portion of the data elements.

18. The computer program product of claim 14, further comprising computer-executable instructions that, when executed, cause the computer system to structure messages including the modified response according to proprietary message definitions.

19. The computer program product of claim 14, further comprising computer-executable instructions that, when executed, cause the computer system to structure messages including the modified response according to industry standard message definitions.

20. The computer program product of claim 19, wherein computer-executable instructions that, when executed, cause the computer system to structure messages including the modified response according to industry standard message definitions comprise computer-executable instructions that, when executed, cause the computer system to structure messages including the modified response according to the HL7 protocol.

21. A computer program product for use at an expert system separate from a clinical system and configured to communicate with the clinical system, the computer program product for implementing a method of providing clinical decision support, notwithstanding that the separate expert system and the clinical system are configured to process data having different and otherwise incompatible data formats, the computer program product comprising one or more physical storage media have stored thereon computer-executable instructions that, when executed at a processor, cause the system to perform the method, including the following:

allow access to an expert system user interface;

provide an element in the expert system user interface for selecting at least one patient from patients in a clinical system;

generate a patient specific recommendation; receiving orders from a user accessing the expert system user interface, the order having a first format structured for compatible processing at the expert system;

process the order to generate a response to the order, the response having the first data format structured for compatible processing at the separate expert system;

modify the structure of the response to a second different format such that the response can be compatible processed at the clinical system, wherein without the structural modification of the response the clinical system is unable to compatibly process the response; and send the modified response to the clinical system on at least one of the synchronous alert interface, an outbound data interface and an outbound orders interface.

22. The computer program product of claim 21, further comprising computer-executable instructions that, when executed at a processor, cause the system to:

receive updates to clinical data from a user accessing the expert system user interface; and send the updates to the clinical system on an outbound data interface.

23. The computer program product of claim 22, wherein computer-executable instructions that, when executed at a processor, cause the system to send the updates to the clinical system comprise computer-executable instructions that, when executed at a processor, cause the system to send the updates directly to a clinical module within the clinical system.

24. The computer program product of claim 22, wherein computer-executable instructions that, when executed at a processor, cause the system to send the updates comprise computer-executable instructions that, when executed at a processor, cause the system to send the updates to a clinical system interface engine for delivery to a clinical module within the clinical system.

25. The computer program product of claim 21, wherein computer-executable instructions that, when executed at a processor, cause the system to provide an element in the expert system user interface comprise computer-executable instructions that, when executed at a processor, cause the system to provide an element in the expert system user interface for selecting at least one patient from at least one of a list of patients, an alert, or a query.

26. The computer program product of claim 21, further comprising computer-executable instructions that, when executed, cause the computer system to structure messages including the modified response according to proprietary message definitions.

27. The computer program product of claim 21, further comprising computer-executable instructions that, when executed, cause the computer system to structure messages including the modified response according to industry standard message definitions.

28. The computer program product of claim 21, wherein computer-executable instructions that, when executed, cause the computer system to structure messages including the modified response according to industry standard message definitions comprise computer-executable instructions that, when executed, cause the computer system to structure messages including the modified response according to the HL7 protocol.

* * * * *

UNITED STATES PATENT AND TRADEMARK OFFICE
CERTIFICATE OF CORRECTION

| | | |
|---|---|---|
| PATENT NO. | : 7,705,727 B2 | Page 1 of 5 |
| APPLICATION NO. | : 11/747817 | |
| DATED | : April 27, 2010 | |
| INVENTOR(S) | : Stanley L. Pestotnik et al. | |

It is certified that error appears in the above-identified patent and that said Letters Patent is hereby corrected as shown below:

The title page should be deleted to appear as per attached title page.

The sheets of drawing consisting of figures 1, 4 and 8 should be deleted to appear as per attached figures 1, 4 and 8.

Sheet 8, replace Figure 8 with the figure attached, wherein the box entitled "Clinical Systems CS" has been incorrectly labeled "401" and has been changed to --801--

Signed and Sealed this
Tenth Day of July, 2012

David J. Kappos
*Director of the United States Patent and Trademark Office*

(12) United States Patent
Pestotnik et al.

(10) Patent No.: US 7,705,727 B2
(45) Date of Patent: Apr. 27, 2010

(54) SYSTEM, METHOD, AND COMPUTER PROGRAM FOR INTERFACING AN EXPERT SYSTEM TO A CLINICAL INFORMATION SYSTEM

(75) Inventors: Stanley L. Pestotnik, Sandy, UT (US); William J. Ketcherside, Jr., Kansas City, MO (US); Jonathan B. F. Olson, Salt Lake City, UT (US); William F. Harty, Salt Lake City, UT (US); Robert R. Hausam, Midvale, UT (US); Michael E. Baza, Woods Cross, UT (US)

(73) Assignee: TheraDoc, Inc., Salt Lake City, UT (US)

( * ) Notice: Subject to any disclaimer, the term of this patent is extended or adjusted under 35 U.S.C. 154(b) by 230 days.

(21) Appl. No.: 11/747,817

(22) Filed: May 11, 2007

(65) Prior Publication Data
US 2007/0213602 A1    Sep. 13, 2007

Related U.S. Application Data

(63) Continuation of application No. 10/773,106, filed on Feb. 5, 2004, now Pat. No. 7,230,529.

(60) Provisional application No. 60/445,889, filed on Feb. 7, 2003.

(51) Int. Cl.
*G08B 1/00* (2006.01)

(52) U.S. Cl. .................. 340/539.12; 702/2; 702/3
(58) Field of Classification Search ........... 340/539.12, 340/286.02; 702/2, 3
See application file for complete search history.

(56) References Cited

U.S. PATENT DOCUMENTS 5,517,405 A * 5/1996 McAndrew et al. .......... 706/45

FOREIGN PATENT DOCUMENTS

WO    WO 00/07339    9/2000

OTHER PUBLICATIONS

EPO Supplementary Search Report from European Application No. 04709070.9, dated Sep. 23, 2009, 5 pages.

(Continued)

*Primary Examiner*—Daryl C Pope
(74) *Attorney, Agent, or Firm*—Workman Nydegger

(57) ABSTRACT

A method and computer program for interfacing an expert system to a clinical information system. Embodiments of the invention provide tight integration of the systems permitting a clinician to use the functionality provided by the expert system without specifically maintaining separate patient data. They provide a method for communication between the expert system and one or more clinical information systems. This communication permits flow of information and actions between the expert system and the clinical systems and allows maintenance of audit logs in both systems.

28 Claims, 9 Drawing Sheets